(12) United States Patent
Edell et al.

(10) Patent No.: US 6,643,552 B2
(45) Date of Patent: Nov. 4, 2003

(54) IMPLANTABLE DEVICES HAVING A LIQUID CRYSTAL POLYMER SUBSTRATE

(75) Inventors: David J. Edell, Lexington, MA (US); Brian Farrell, Quincy, MA (US)

(73) Assignees: Foster-Miller, Inc., Waltham, MA (US); Innersea Technology, Bedford, MA (US)

( * ) Notice: Subject to any disclaimer, the term of this patent is extended or adjusted under 35 U.S.C. 154(b) by 0 days.

(21) Appl. No.: 10/158,510

(22) Filed: May 30, 2002

(65) Prior Publication Data

US 2002/0198582 A1 Dec. 26, 2002

Related U.S. Application Data

(60) Provisional application No. 60/294,348, filed on May 30, 2001.

(51) Int. Cl.$^7$ ................................................. A61N 1/05
(52) U.S. Cl. ...................... 607/116; 607/119; 607/152; 607/117; 607/148; 600/393; 600/373
(58) Field of Search ................................ 607/116, 117, 607/119, 129, 137, 148, 152; 600/373, 378, 393, 395, 377

(56) References Cited

U.S. PATENT DOCUMENTS 5,063,081 A  * 11/1991 Cozzette et al. ................ 435/4
5,169,397 A  * 12/1992 Sakashita et al. ............. 606/27
6,463,334 B1 * 10/2002 Flynn et al. ................. 607/127

* cited by examiner

*Primary Examiner*—Kennedy Schaetzle
(74) *Attorney, Agent, or Firm*—Weingarten, Schurgin, Gagnebin & Labovici LLP

(57) ABSTRACT

An implantable medical device (IMD) is disclosed that is formed on a substrate composed of liquid crystal polymer (LCP). In one embodiment, the IMD can be an interconnection module for interconnecting an electrode array to an equipment module. The interconnecting module includes conductors disposed on the LCP substrate and coupled to the electrode array, and wherein the conductors are encapsulated using a silicone or LCP encapsulant. In another embodiment, the IMD is an electrode array and interconnect module disposed on an integral LCP substrate. An equipment module can be coupled to the interconnect module. Alternatively, a hybrid electronic circuit can be coupled to the interconnect module for signal processing and conditioning signals received from the electrode array or for providing stimulus signals to the electrode array. In this embodiment, all of the conductors and at least a portion of the electrodes in the electrode array are encapsulated using a silicone or LCP encapsulant. In another embodiment, the IMD is an electrode array, an interconnecting module, and a hybrid circuit that are disposed on an LCP substrate. The interconnecting module is used to provide signal paths to and from the electrodes in the electrode array to the hybrid circuit. In this embodiment, all of the conductors, the hybrid electronic circuit and at least a portion of the electrodes in the electrode array are encapsulated using a silicone or LCP encapsulant.

58 Claims, 5 Drawing Sheets

IMPLANTABLE DEVICES HAVING A LIQUID CRYSTAL POLYMER SUBSTRATE

CROSS REFERENCE TO RELATED APPLICATIONS

This application claims priority under 35 U.S.C. §119(e) to provisional patent application ser. No. 60/294,348 filed May 30, 2001, the disclosure of which is incorporated by reference herein.

STATEMENT REGARDING FEDERALLY SPONSORED RESEARCH OR DEVELOPMENT

N/A

BACKGROUND OF THE INVENTION

This invention relates generally to implantable electrodes and electronic hybrid circuits and in particular to implantable electrodes and electronic hybrid circuits having a liquid crystal substrate.

Microelectronic components, integrated circuits, and implantable electrodes are used extensively in implantable medical devices (IMDs) such as cardiac pacemakers, cochlear prosthesis devices, and neuroprostheses. IMDs can be constructed using a variety of well known methods such as printed circuit boards and hybrid circuits formed on a substrate. Typical hybrid circuits are used can be formed using well known techniques. As the device size and conductor size decrease to below approximately 10 micrometers, the hybrid substrate must be micro-machined using photolithographic techniques to pattern and put down the conductor traces. An IMD needs to be encased with an encapsulant such as silicone that is chemically bonded to the substrate.

Implanting medical devices in a biological environment subjects the IMD to a chemically and electrically harsh environment. For example, the biological environment is highly corrosive to many materials, and the conductors used to connect the device to other electronic circuits or connectors must be able to withstand immersion in an ionic fluid with as much as a 10-volt bias across it.

Cardiac pacemakers typically include a hermetically sealed titanium canister containing the power source and associated circuitry and glass sealed electrode feed-throughs to allow the electronic signals generated by the circuitry to interface to the heart muscle. The size of cardiac pacemakers is dominated by the size of the energy source, and typically, the titanium case is a few centimeters in diameter and half a centimeter thick. The leads are typically multi-filament coils of a high nickel content stainless steel alloy and the leads are typically insulated with using silicone. Silicone insulated leads have been very reliable, however, silicone has a tendency to stick to tissue during insertion and to reduce the diameter of the pacemaker leads.

IMDs for neuroprostheses have even more demanding requirements than cardiac pacemakers. Neuroprostheses for rehabilitation of the deaf, blind, spinal cord injured and amputees are being developed that make use of IMDs. In these instances, the IMD requires close proximity to the small and fragile cells of the nervous system. In some cases, the IMDs will be attached or embedded directly in the neural tissue. The neural tissue is a very dynamic environment, for example peripheral nerves stretch and relax with the motion of a limb, the spinal cord moves within the spinal canal, the brain moves relative to the skull any motion of the head and also with each heartbeat, and movement of the eyes creates substantial acceleration forces on the retina.

Because of the nature of the biological environment, the fragile nature of the neural tissue, the high packing density of the neural tissue, the effects of dissimilar acceleration, and the proliferation of connective tissue that can encase an IMD, IMDs used as neuroprostheses must be biocompatible, bioresistant, be of small size, be density matched to the surrounding neural tissue and be minimally tethered to the surrounding tissue.

Biocompatibility is essential in an IMD to minimize the formation of connective tissue between the nearby neurons and the IMD over the course of long term or chronic implantation. Bioresistance, or chemical inertness with respect to the biological environment is essential to prevent corrosion from damaging the IMD. An IMD needs a small size to minimize damage to the target neural structures during implantation. To avoid differential acceleration between the IMD and the surrounding tissue, matching the density of the two is important to avoid damage to the surrounding tissue. Minimal tethering between an electrode and an electronic device will reduce the transmission of forces transmitted along the wiring between the electronic device and the implanted electrode, particularly after being encased in connective tissue as part of the normal healing process.

Silicon has been the material of choice for neuroprosthetic IMDs because of its mechanical and chemical properties. For example, silicon can be micro-machined to extraordinarily small dimensions, is very strong, relatively corrosion resistant, can have embedded integrated circuits for signal processing or controlling functions, and because it forms an inert self limiting oxide that is biocompatible. Silicon may be micro-machined to produce a variety of novel structures. Silicones are an important class of materials that can both insulate silicon substrates as well as protect silicon substrates from corrosive environments. However, although silicone has been shown useful as an encapsulant, silicone has not been useful as a micro-machined substrate because it is not dimensionally stable and thus cannot support fine metal patterns or be photolithographically processed.

Of the many candidate materials that have been used in the prior art, only polyimide was a possible polymer that could be used for flexible implantable microelectrode array substrates. Polyimide has been used extensively by researchers for producing microelectrode arrays for cochlear electrode arrays, retinal prostheses, peripheral nerve electrodes, and central nerve electrodes. While polymer based flexible electrodes have been previously developed using polyimide, polyimide is not a very long-term water resistant material. Furthermore, polyimide is used as a sensor for humidity because of its hygroscopic quality. Although polyimide structures may be able to withstand up to several years of static immersion in saline, the failure modes of polymide structures are usually linked to mechanical weakening of the material due to hydrolytic attack.

Micro-machined silicon substrates as fabricated are not bioresistant and can have multiple failure modes when an integrated circuit or microelectronic hybrid circuit are formed thereon. The wires used to attach to the circuit elements must be able to withstand immersion in ionic fluids. Exposed areas where the wires are attached to connectors or devices are coated with encapsulant material that is applied after wire bonding as been accomplished. If micro-ribbon technology is used, it is necessary to create a void free seal in the area under the micro-ribbon attached to the device. Circuits on the chip must be protected from water and ionic contamination and the chip substrate and encapsulants must be bioresistant and biocompatible.

Therefore, it would be advantageous to provide a substrate and/or encapsulant for an IMD that has is biocompatible, bioresistant, small size, and has a density that is matched to the surrounding neural tissue.

BRIEF SUMMARY OF THE INVENTION

An implantable medical device (IMD) is disclosed that is formed on a substrate composed of liquid crystal polymer (LCP). In one embodiment, the IMD can be an interconnection module for interconnecting an electrode array to an equipment module. The interconnecting module includes conductors disposed on the LCP substrate and coupled to the electrode array, and wherein the conductors are encapsulated using a silicone or LCP encapsulant. In another embodiment, the IMD is an electrode array and interconnect module disposed on an integral LCP substrate. An equipment module can be coupled to the interconnect module. Alternatively, a hybrid electronic circuit can be coupled to the interconnect module for signal processing and conditioning signals received from the electrode array or for providing stimulus signals to the electrode array. In this embodiment, all of the conductors and at least a portion of the electrodes in the electrode array are encapsulated using a silicone or LCP encapsulant. In another embodiment, the IMD is an electrode array, an interconnecting module, and a hybrid circuit that are disposed on an LCP substrate. The interconnecting module is used to provide signal paths to and from the electrodes in the electrode array to the hybrid circuit. In this embodiment, all of the conductors, the hybrid electronic circuit and at least a portion of the electrodes in the electrode array are encapsulated using a silicone or LCP encapsulant.

Other forms, features and aspects of the above-described methods and system are described in the detailed description that follows.

BRIEF DESCRIPTION OF THE SEVERAL VIEWS OF THE DRAWING

The invention will be more fully understood from the following detailed description taken in conjunction with the accompanying drawings in which.

DETAILED DESCRIPTION OF THE INVENTION

Figure 1:
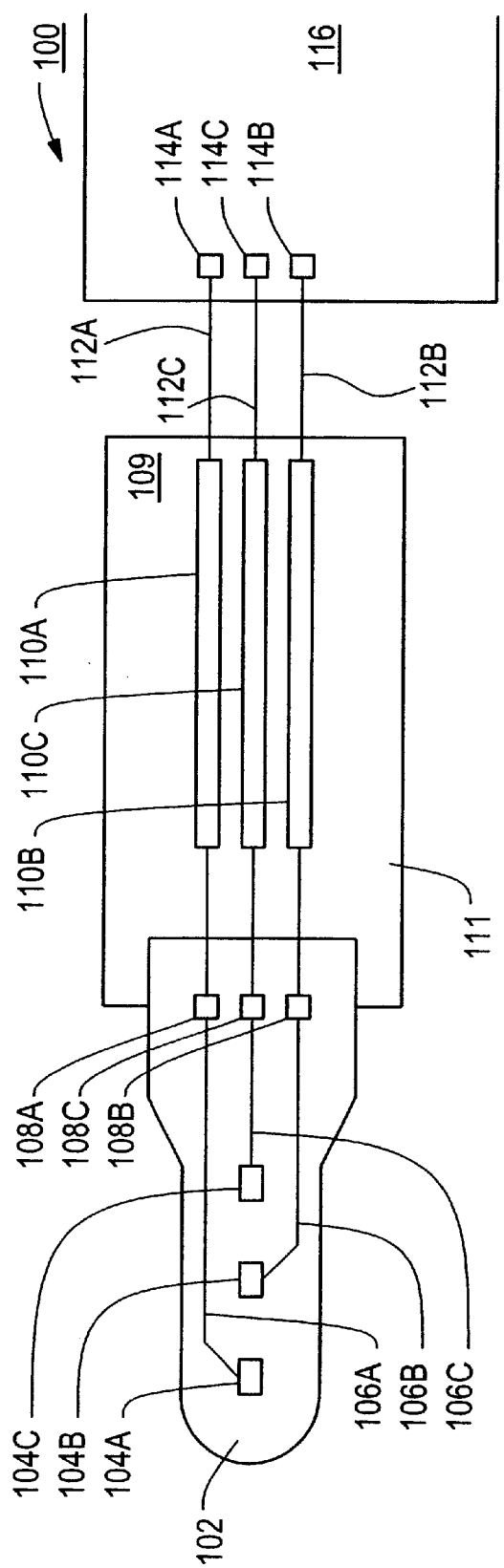
FIG. 1 is a top schematic view of an electrode array module and an LCP interconnect module.

Liquid crystal polymers (LCP) are so called because their molecules can be mutually aligned and organized (crystal), yet the bulk LCP can flow (liquid) in the molten state. This behavior is unlike ordinary polymers that are randomly configured in the melt or in solution. The liquid crystal state results from the rigid nature of segments of the LCP molecules. When the LCP flows in the liquid crystal state, the rigid segments of the molecules align next to one another in the shear flow direction, creating locally oriented domains. The domains in turn create macroscopic oriented regions. Once the oriented regions are formed, their direction and structure persist, even when the LCP approaches the melt temperature, because of the long relaxation time of the stiff chain LCP molecules. All commercial LCPs are copolymers composed of molecules with rigid and flexible monomeric units.

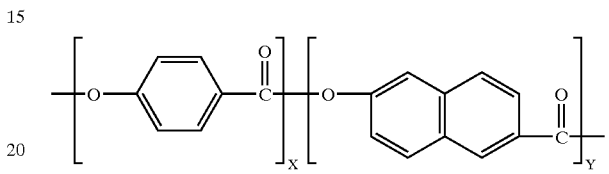

The ratio of the rigid monomer, X, to the flexible monomer, Y, as shown above, determines the properties of the LCP material.

The high degree of molecular order that can be achieved with the LCP molecules at a supramolecular level results in a self-reinforced structure with outstanding strength, stiffness, and chemical barrier properties. Traditional processing of LCPs has not resulted in a product suitable for electronic packaging applications however because of anisotropic tensile strength. Foster-Miller has developed processing technology that permits control of the fibrillar LCP orientation to any desired value, including quasi-isotropic, simply by varying the processing parameters. By utilizing a novel annular die, sheet and films can be produced with controlled directions of orientation. When LCPs are processed into ±45° biaxial films, physical properties such as CTE, tensile strength and modulus are near isotropic. The resulting biaxially oriented LCP materials have unique properties.

For example, LCP dielectrics can also provide near hermetic packaging due to their low moisture and oxygen permeability. Although random films exhibit good chemical barrier properties, biaxially oriented films show orders of magnitude lower values. The water permeability of oriented LCP films is comparable to glasses. This unique property indicates the use of LCP substrate for both electrical interconnection and as an effective barrier to moisture.

In addition, LCPs used in in-vivo environments have been shown to be biocompatible per USP, to have a flexural fatigue resistance that is in excess of $50 \times 10^6$ flex cycles. LCPs have also been shown to have saline soak resistance with no evidence of degradation in mechanical properties being observed after five months in physiological saline solution.

LCP is a unique material that satisfies the constraints of constructing implantable microelectronic devices where size and flexibility issues are of importance. LCP has applications not only as a substrate material for supporting microfabricated thin film interconnects, but also for implantable, flexible circuit board material and even device encapsulation.

LCPs have a unique combination of properties that make them highly adaptable to medical applications, for example LCPs have a low dielectric constant, 2.9, and low dielectric loss tangent (0.002) for electrical performance. LCPs exhibit excellent dimensional stability and support interconnect lines and spaces as small as 50 μm on large substrates and 10 μm on small (less that 6" diameter) substrates. The thermal coefficient of LCP is low, similar to that of silicon, and LCP is unaffected by common solvents, household and industrial chemicals, oils, and hydrocarbons. LCPs have not shown degradation in their mechanical properties during prolonged exposure to Ringer's solution. The barrier properties of LCP materials is comparable to that of glass so that LCPs are virtually impermeable to moisture, oxygen, and other gases and liquids, and the maximum water absorption by LCPs is less than 0.02 percent.

FIG. 1 depicts a top view of a combination of an electrode array module 102 and an LCP substrate based interconnect module 104. In particular, the electrode array module 102 includes a plurality of electrodes 104A, 104B, and 104C formed on the surface of a substrate 103. Conductors 106A, 106B, and 106C are disposed on the surface of the substrate 103 and are electrically connected to a corresponding electrode. The substrate 103 of the electrode array module 102 can be silicon or LCP.

Each of the conductors 106A–106C is further electrically coupled to a corresponding electrical interconnection bonding pad 108A–108C that is used to provide the signals to a corresponding conductor 110A–110C on an LCP interconnect module 109. The conductors 110A–110C are disposed on the surface of the LCP substrate 111 that forms the LCP interconnect 109. The conductors 110A–110C are coupled at the distal end of the LCP interconnect module 109 to an equipment module 116 via conductors 112A–112C and connectors 114A, 114B, and 114C respectively. The equipment module may be for example, a percutaneous connector that may include electronic components or circuits, a telemetry module, or other instrumentation.

Figure 2:
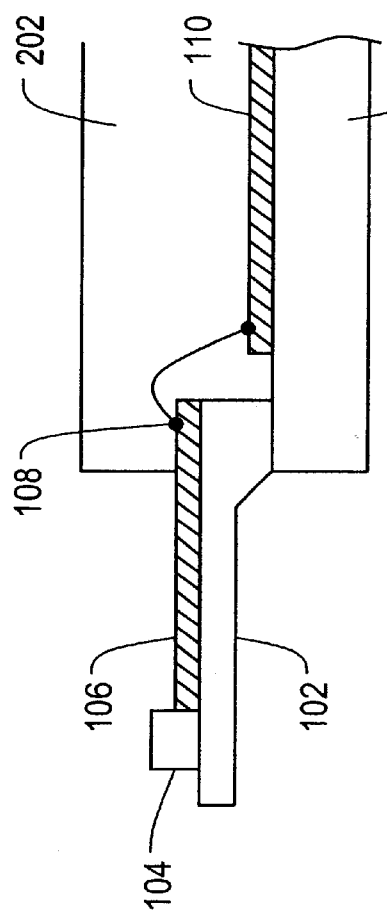
FIG. 2 is a side cross-sectional view of the interconnection between the electrode array module and the LCP interconnect module depicted in FIG. 1.

FIG. 2 depicts a side cross-sectional view of the combination of the electrode array module 102 and the LCP substrate based interconnect 104. As shown in FIG. 2, the electrode array module 102 includes the electrode 104 formed on a substrate 103 and connected to a conductor 106 that is also formed on the surface of the LCP substrate 103. A portion of the electrode 104 and the conductor 106 are encapsulated by a coating 202 that is disposed on and chemically bonded to the surface of LCP substrate 103. In this way, the conductors are protected from the external environment that can include the interior of a body after being implanted therein. In one embodiment, the encapsulant is LCP, while in another embodiment, the encapsulant is silicone. The encapsulant can be coated using a variety of coating methods such as by plasma deposition, by brush, dip, spray, or spin coating from a liquid silicone rubber (LSR) mixture. In the case of spin coating the LSR would preferably be a platinum catalyzed material that is a room temperature vulcanizable (RTV) LSR. A peroxide or tin catalyzed LSR can also be used.

The conductor 106 is coupled to the corresponding electrical interconnection bonding pad 108, and via conductor 204 to the corresponding conductor 106 that is formed on the LCP substrate based interconnect module 109. The conductor 110 is disposed on the surface of the LCP substrate 111 that forms the LCP interconnect module 109. In the embodiment depicted in FIG. 2 the LCP electrode module 102 is affixed to the top surface of the LCP interconnect module 109. The conductor 110 is encapsulated by a coating 202 that is disposed on and chemically bonded to the surface of LCP substrate 111. In this way, the conductors 110 are protected from the external environment that can include the interior of a body after being implanted therein. In one embodiment, the encapsulant is silicone, while in another embodiment, the encapsulant is an LCP.

Figure 3:
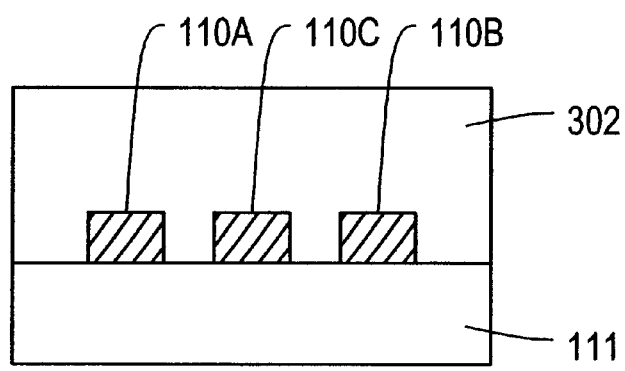
FIG. 3 is a front cross-sectional view of the LCP interconnect module depicted in FIG. 1.

FIG. 3 depicts a front cross-sectional view of the LCP substrate based interconnect module 109. The three conductors 110A–110C are disposed on the surface of the LCP substrate 111 and encapsulated by encapsulant 206 as described above.

For the embodiments depicted in FIGS. 1–4 the number of electrodes and conductors are shown for illustrative purposes only. Any number of electrodes and conductors can be formed and the actual number is dependent upon the application requirements. In addition, although a generally rectangular shape is depicted, the LCP electrode module 102 and the interconnect module 109 can be formed into arbitrary shapes. The actual shape that is used will be dependent upon the application requirements.

Figure 4:
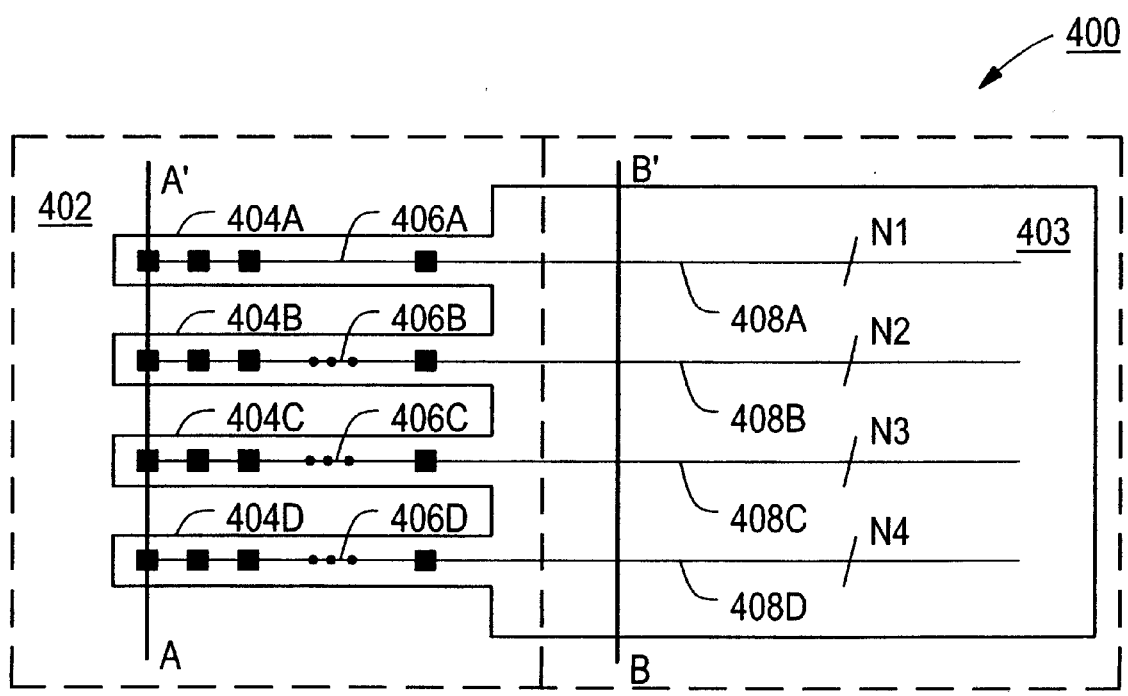
FIG. 4 is a top schematic view of an integral electrode array and interconnect module using an LCP substrate.

FIG. 4 depicts an integral electrode array and interconnect module using an LCP substrate. In particular, a single piece of LCP substrate 401 is used to form an electrode array portion 402 and an interconnect portion 403. The electrode array portion 402 can include one or more electrode shafts 404A–404D, each of which contains one or more electrodes 406A–406D respectively. Each electrode is coupled to one or more conductors 408A–40D respectively, that are provided to couple electrical signals to and from the respective electrode. The number of electrodes on each shaft 404A–404D is arbitrary and can be adjusted to any predetermined number according to the application requirements. In the illustrated embodiment, there are N1 electrodes on shaft 404A each coupled to a corresponding one of N1 conductors contained in conductor 408A. Similarly, there are N2 electrodes on shaft 404B each coupled to a corresponding one of N2 conductors contained in conductor 408B. There are N3 electrodes on shaft 404C each coupled to a corresponding one of N3 conductors contained in conductor 408C and, N4 electrodes on shaft 404D each coupled to a corresponding one of N4 conductors contained in conductor 408D.

Figure 5:
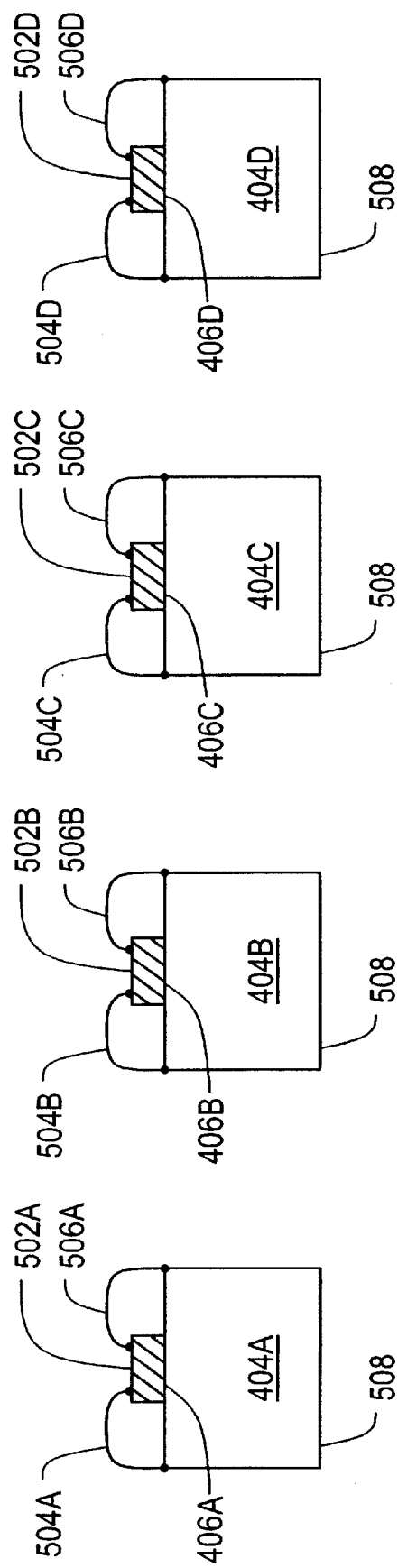
FIG. 5 is a cross-sectional view of the integral electrode array and interconnect module of FIG. 4 along line A–A'.

FIG. 5 depicts a cross-sectional view of the electrode module 400 of FIG. 4 taken along line B–B' in FIG. 4. Each of the shafts 404A–404D are depicted in cross-section and illustrate that each electrode 406A–406D is formed on the surface of the LCP substrate 508 and includes a portion 502A–502D that is not encapsulated by encapsulant 504A–504D and 506A–506D.

Figure 6:
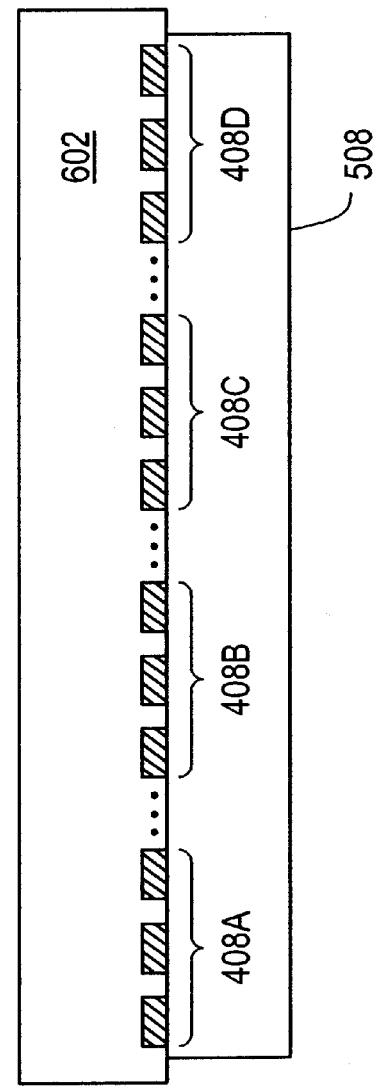
FIG. 6 is a cross-sectional view of the integral electrode array and interconnect module of FIG. 4 along line B–B'.

FIG. 6 depicts a cross-sectional view of the electrode module 400 taken along C–C' in FIG. 4. Each of the conductors 408A–408D are disposed on the surface of the LCP substrate 508 and are encapsulated by encapsulant 602. As discussed above, the conductors 408A–408D are encapsulated by a coating 602 that is disposed on and chemically bonded to the surface of LCP substrate 508. In this way, the encapsulant protects the conductors 408A–408D from the external environment that can include the interior of a body after being implanted therein. In one embodiment, the encapsulant is LCP, and in another embodiment, the encapsulant is silicone.

Figure 7:
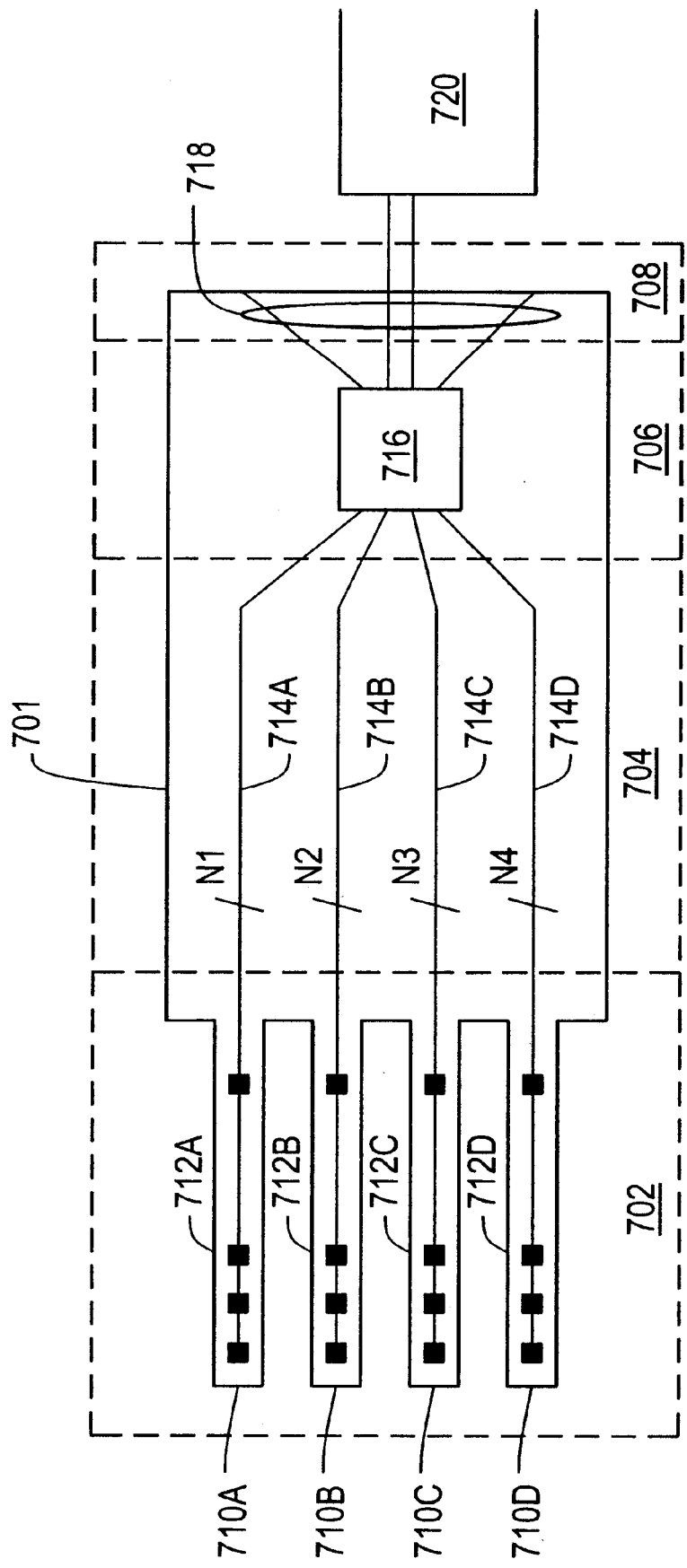
FIG. 7 is a top schematic view of an integral electrode array, interconnect module and hybrid electronic circuit using an LCP substrate.

FIG. 7 depicts an integral electrode array, interconnect module, hybrid electronic circuit, and output portion using an LCP substrate. In particular, an LCP substrate 701 is used as the substrate for an electrode array portion 702, an interconnect portion 704, a hybrid electronic circuit portion 706, and an output portion 708. The electrode array portion 702 can include one or more electrode shafts 710A–710D, each of which contains one or more electrodes 712A–712D respectively. Each electrode is coupled to one or more conductors 714A–714D respectively, that are provided to couple electrical signals to and from the respective electrode. The number of electrodes on each shaft 704A–704D is arbitrary and can be adjusted to any predetermined number according to the application requirements. In the illustrated embodiment, there are N1 electrodes on shaft 710A each coupled to a corresponding one of N1 conductors contained in conductor 714A. Similarly, there are N2 electrodes on shaft 710B each coupled to a corresponding one of N2 conductors contained in conductor 714B. There are N3 electrodes on shaft 710C each coupled to a corresponding one of N3 conductors contained in conductor 714C and, N4 electrodes on shaft 710D each coupled to a corresponding one of N4 conductors contained in conductor 714D. At least some of the conductors 74A–714D are electrically coupled to the hybrid circuit 716. The hybrid circuit 716 is electrically can be coupled to one or more output conductors 718 that are coupled to an equipment module 720. The equipment module 720 may be for example, a percutaneous connector that may include other electronic components or circuits, a telemetry module, or other instrumentation. The hybrid circuit can be used to provide signal conditioning and processing of signals received from one or more of the electrodes in the electrode array or prior to providing the signal to the equipment module. The hybrid circuit 716 can also be used to provide signal conditioning, amplification, or processing of signals to be transmitted from the equipment module 720 to one or more of the electrodes as a stimulation signal. The hybrid circuit 716, the conductors 714A–714D and 718, and a portion of each of the electrodes 712A–712D are encapsulated by an encapsulation material that is chemically bonded to the LCP substrate. In one embodiment, the encapsulant material is silicone and in another embodiment the encapsulant material is LCP.

Alternatively, the hybrid circuit can be external to the integral electrode array and interconnect module. In this embodiment, the hybrid circuit is encapsulated and is connected via encapsulated conductors electrically connected to the interconnect portion of the integral LCP substrate. The hybrid circuit then provides encapsulated conductors to the equipment module that is discussed above with respect to FIG. 7.

Figure 8:
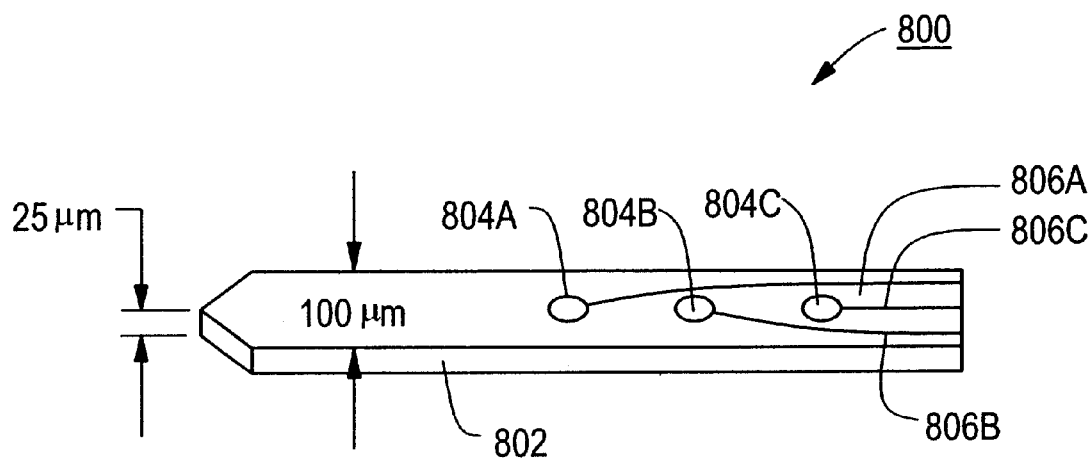
FIG. 8 is a perspective view of a micro-wire electrode array.

FIG. 8 depicts a micro-wire electrode array using an LCP substrate. The micro-wire electrode 800 includes a LCP substrate 802 that is approximately 25 micrometers thick and approximately 100 micrometers wide. At least one electrode, and more commonly a plurality of electrodes 804A, 804B, and 804C are disposed on the surface of the LCP substrate 802. Each electrode 804A–804C is electrically connected to a corresponding electrical interconnect conductor 806A, 806B, and 806C respectively.

Figure 9:
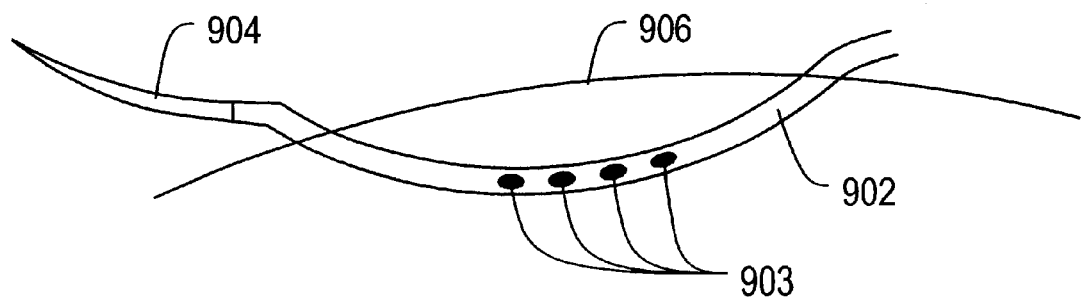
FIG. 9 is a side cross sectional view of a micro-wire array being inserted into and threaded through cortical tissue.

FIG. 9 depicts a micro-wire electrode array 902 having electrodes 903 as described above attached to a surgical needle 904 and being inserted into and threaded internal cortical structures 906 using the surgical needle 904. The micro-wire electrode array is attached to the surgical needle 904 and inserted into the cortical tissue to a predetermined depth corresponding to an appropriate layer of the cortical tissue, for example layer 4, in order to receive signals from the surrounding cortical tissue or to stimulate the surrounding cortical tissue.

For the embodiments depicted herein for microelectrode arrays having a plurality of shafts, the shafts typically are 10–40 $\mu$m thick and 40–200 $\mu$m wide and a few millimeters when used for sensing or stimulating cortical cells and several centimeters long when used for sensing or stimulating deeper brain/spinal cord structures. The spacing between the shafts is typically between 100–200 $\mu$m. Typically electrode contacts are 10–1000 $\mu$m$^2$, but will be bigger when the contacts are used to stimulate larger groups of neurons or other bodily structures. The spacing between electrodes is typically greater than or equal to 50 $\mu$m, although some protocols require very closely spaced electrodes having a edge to edge distance between adjacent electrodes of as little as 10 $\mu$m.

In the embodiments described herein, the LCP substrate is micro-machined to receive conductor traces. The micromachining typically uses one of two known methods. The first method, the "lift-off" method, involves pre-coating the substrate with photoresist and patterning the photoresist in desired conductor traces using standard masking and exposure techniques to expose the LCP substrate where the conductor traces are desired. Unwanted metal is then "lifted off" by dissolving the remaining photoresist using a solvent, leaving the remaining conductor material in the desired configuration.

The second technique is to deposit metal over the entire surface of the LCP substrate, and pattern the metal using standard photoresist, masking, and exposure techniques. The unwanted metal is then etched away using a variety of standard techniques, leaving the remaining conductor in the desired configuration.

In either technique described above, the conductor material can be deposited on the patterned surface of the LCP substrate by any of several known methods of deposition such as electroplating, evaporating, sputtering, or other deposit techniques known in the art. In addition, contact holes for bonding or electrode contacts can be etched into the surface or laser ablation and coated with appropriate conductive materials.

Those of ordinary skill in the art should further appreciate that variations to and modification of the above-described apparatus for providing an implantable device within a body cavity may be made without departing from the inventive concepts disclosed herein. Accordingly, the invention should be viewed as limited solely by the scope/spirit of the appended claims.

What is claimed is:

1. An implantable electrode and interconnect module comprising:

a first substrate;

a second substrate composed of LCP;

the first substrate including at least one electrode conductor disposed thereon and an associated interconnect conductor disposed thereon electrically connected to the electrode conductor;

the second substrate including an electrical interconnection bonding pad electrically coupled to the interconnect conductor of the first substrate and a conductor electrically connected to the interconnection bonding pad;

a first encapsulant covering a portion of the electrode conductor and completely covering the interconnect conductor, the first encapsulant chemically bonded to the first substrate, wherein the portion of the electrode conductor and the interconnect conductor are protected from an external environment; and a second encapsulant completely covering the interconnect conductor and the electrical interconnection bonding pad, the second encapsulant chemically bonded to the second substrate, wherein the interconnect conductor and the electrical interconnection bonding pad are protected from an external environment.

2. The implantable electrode of claim 1 wherein the first substrate is silicon.

3. The implantable electrode of claim 1 wherein the first substrate is LCP.

4. The implantable electrode of claim 1 wherein the first encapsulant is silicone.

5. The implantable electrode of claim 1 wherein the first encapsulant is LCP.

6. The implantable electrode of claim 1 wherein the second encapsulant is silicone.

7. The implantable electrode of claim 1 wherein the second encapsulant is LCP.

8. The implantable electrode of claim 1 wherein the electrical interconnection bonding pad is electrically coupled to the interconnect conductor of the first substrate via an encapsulated conductor.

9. The implantable electrode of claim 1 further including an equipment module electrically coupled to the conductor of the second substrate.

10. The implantable electrode of claim 9 wherein the equipment module is electrically coupled to the conductor of the second substrate via an encapsulated conductor.

11. The implantable electrode of claim 9 wherein the equipment module is a percutaneous connector.

12. The implantable electrode of claim 11 wherein the percutaneous connector includes a percutaneous substrate that is LCP.

13. The implantable electrode of claim 9 wherein the equipment module is a telemetry module.

14. The implantable electrode of claim 13 wherein the telemetry module includes a substrate that is LCP.

15. The implantable electrode of claim 9 wherein the equipment module includes a equipment module substrate that is LCP.

16. The implantable electrode of claim 1 further including a hybrid electronic circuit electrically coupled to the conductor of the second substrate.

17. The implantable electrode of claim 16 wherein the hybrid electronic circuit is electrically coupled to the conductor of the second substrate via an encapsulated conductor.

18. The implantable electrode of claim 16 further including an equipment module electrically coupled to the hybrid electronic circuit.

19. The implantable electrode of claim 18 wherein the equipment module is electrically coupled to the hybrid electronic circuit via an encapsulated conductor.

20. The implantable electrode of claim 19, wherein the equipment module includes an LCP substrate.

21. The implantable electrode of claim 18, wherein the equipment module includes an LCP substrate.

22. The implantable electrode of claim 16 wherein the hybrid electronic circuit includes a hybrid substrate that is LCP.

23. The implantable electrode of claim 22 wherein the hybrid substrate is integral with the second substrate.

24. An electrode array comprising:
an LCP substrate having an electrode portion and an interconnect portion;
an electrode disposed on the surface of the electrode portion of the LCP substrate;
an electrode interconnect conductor disposed on the electrode portion of the LCP substrate, the conductor electrically connected to the electrode;
an interconnect conductor formed on the interconnect portion of the LCP substrate, the interconnect conductor electrically connected to the electrode interconnect conductor;
an encapsulant covering the interconnect conductor formed on the interconnect portion of the LCP substrate, the electrode interconnect conductor formed on the electrode portion of the LCP substrate, and covering a portion the electrode formed on the electrode portion of the LCP substrate, the encapsulant chemically bonded to the LCP substrate, wherein the encapsulated electrode interconnect conductor, the encapsulated interconnect conductor and the encapsulated portion of the electrode are protected from an external environment.

25. The electrode array of claim 24 wherein the electrode portion of the LCP substrate includes two or more shafts formed with the LCP substrate, and each of the at least two shafts includes at least one electrode disposed on the surface of the respective shaft, and wherein the electrode interconnect conductor includes a number of electrode interconnect conductors corresponding to the number of electrodes, and wherein the interconnect conductor includes a number of interconnect conductors corresponding to the number of electrode interconnect conductors.

26. The electrode array of claim 25 wherein the encapsulant is a silicone encapsulant.

27. The electrode array of claim 25 wherein the encapsulant is an LCP encapsulant.

28. The electrode array of claim 25 further including an equipment module electrically coupled to at least one of the interconnect conductors.

29. The electrode array of claim 28 wherein the equipment module is electrically coupled to the at least one interconnect conductor via an encapsulated conductor.

30. The implantable electrode of claim 28 wherein the equipment module is a percutaneous connector.

31. The electrode array of claim 30 wherein the percutaneous connector includes a percutaneous substrate that is LCP.

32. The implantable electrode of claim 28 wherein the equipment module is a telemetry module.

33. The electrode array of claim 32 wherein the telemetry module includes a substrate that is LCP.

34. The electrode array of claim 28 wherein the equipment module includes a equipment module substrate that is LCP.

35. The implantable electrode of claim 25 further including a hybrid electronic circuit electrically coupled to at least one interconnect conductor.

36. The implantable electrode of claim 35 wherein the hybrid electronic circuit is electrically coupled to the at least one interconnect conductor via at least one encapsulated conductor.

37. The implantable electrode of claim 36 further including an equipment module electrically coupled to the hybrid electronic circuit.

38. The implantable electrode of claim 37 wherein the equipment module is electrically coupled to the hybrid electronic circuit via an encapsulated conductor.

39. The electrode array of claim 37 wherein the equipment module includes an LCP substrate.

40. The implantable electrode of claim 36 wherein the hybrid electronic circuit includes a hybrid substrate that is composed of LCP.

41. The implantable electrode of claim 40 wherein the hybrid substrate is integral with the second substrate.

42. The electrode array of claim 35 wherein the hybrid electronic circuit includes a hybrid substrate that is composed of LCP.

43. The electrode array of claim 42 wherein the hybrid substrate is integral with the second substrate.

44. An electrode array comprising an LCP substrate having an electrode portion, an interconnect portion, and a hybrid circuit portion;

an electrode disposed on the surface of the electrode portion of the LCP substrate;

an electrode interconnect conductor disposed on the electrode portion of the LCP substrate, the conductor electrically connected to the electrode;

an interconnect conductor formed on the interconnect portion of the LCP substrate, the interconnect conductor electrically connected to the electrode interconnect conductor;

a hybrid circuit disposed on the hybrid circuit portion of the LCP substrate, the hybrid circuit electrically connected to the interconnect conductor formed on the interconnect portion of the LCP substrate;

an encapsulant covering the interconnect conductor formed on the interconnect portion of the LCP substrate, the electrode interconnect conductor formed on the electrode portion of the LCP substrate, the hybrid circuit, and covering a portion the electrode formed on the electrode portion of the LCP substrate, the encapsulant chemically bonded to the LCP substrate, wherein the encapsulated electrode interconnect conductor, the encapsulated interconnect conductor, the hybrid circuit and the encapsulated portion of the electrode are protected from an external environment.

45. The electrode array of claim 44 wherein the electrode portion of the LCP substrate includes two or more shafts formed with the LCP substrate, and each of the at least two shafts includes at least one electrode disposed on the surface of the respective shaft, and wherein the electrode interconnect conductor includes a number of electrode interconnect conductors corresponding to the number of electrodes, and wherein the interconnect conductor includes a number of interconnect conductors corresponding to the number of electrode interconnect conductors.

46. The electrode array of claim 45 wherein the encapsulant is a silicone encapsulant.

47. The electrode array of claim 45 wherein the encapsulant is an LCP encapsulant.

48. The electrode array of claim 45 further including an equipment module electrically coupled to the hybrid circuit.

49. The electrode array of claim 48 wherein the equipment module is electrically coupled to the hybrid circuit via an encapsulated conductor.

50. The electrode array of claim 49 wherein the hybrid electronic circuit includes a hybrid substrate that is composed of LCP.

51. The implantable electrode of claim 50 wherein the hybrid substrate is integral with the LCP substrate.

52. The implantable electrode of claim 48 wherein the equipment module is a percutaneous connector.

53. The electrode array of claim 52 wherein the percutaneous connector includes an LCP substrate.

54. The implantable electrode of claim 48 wherein the equipment module is a telemetry module.

55. The electrode array of claim 54 wherein the telemetry module includes a substrate that is LCP.

56. The electrode array of claim 54 wherein the equipment module includes an LCP substrate.

57. The electrode array of claim 48 wherein the equipment module includes a an LCP substrate.

58. A micro-wire electrode array comprising:

an LCF substrate;

a plurality of electrodes disposed on the surface of the LCP substrate;

a plurality of interconnecting conductors corresponding to the plurality of electrodes, wherein an electrode is electrically connected to a corresponding interconnecting conductor and wherein the LCP substrate is approximately 100 micrometers wide and 25 micrometers thick.

* * * * *

UNITED STATES PATENT AND TRADEMARK OFFICE
CERTIFICATE OF CORRECTION

PATENT NO. : 6,643,552 B2
DATED : November 4, 2003
INVENTOR(S) : David J. Edell et al.

It is certified that error appears in the above-identified patent and that said Letters Patent is hereby corrected as shown below:

Title page,
Item [74], *Attorney, Agent, or Firm*, "Labovici" should read -- Lebovici --;

Column 12,
Line 26, "a an" should read -- an --; and
Line 28, "LCF" should read -- LCP --.

Signed and Sealed this

Second Day of August, 2005

JON W. DUDAS
*Director of the United States Patent and Trademark Office*